United States Patent [19]

Shutske

[11] Patent Number: 5,300,498
[45] Date of Patent: Apr. 5, 1994

[54] 6-PIPERAZINYL-1H-PYRAZOLO[3,4-B]PYRIDINE-3-CARBOXYLIC ACIDS, ESTERS, AMIDES AND RELATED COMPOUNDS

[75] Inventor: Gregory M. Shutske, Flemington, N.J.

[73] Assignee: Hoechst-Roussel Pharmaceuticals Incorporated, Somerville, N.J.

[21] Appl. No.: 71,088

[22] Filed: Jun. 4, 1993

[51] Int. Cl.$^5$ ............... A61K 31/55; A61K 31/495; C07D 471/04
[52] U.S. Cl. .................. 514/218; 514/254; 540/575; 544/360; 544/362; 544/365; 546/119; 546/120; 546/315; 546/335
[58] Field of Search .......... 544/362; 540/575; 514/218, 254

[56] References Cited

U.S. PATENT DOCUMENTS 3,925,388 12/1975 Hoehn et al. ............ 544/362
4,020,072 4/1977 Hoehn ..................... 544/362

OTHER PUBLICATIONS

M. K. A. Ibrahim et al., J. Indian Chem. Soc., vol. 64, 345–347 (1987).

*Primary Examiner*—Emily Bernhardt
*Attorney, Agent, or Firm*—Tatsuya Ikeda

[57] ABSTRACT

There are disclosed various compounds of the formula below,

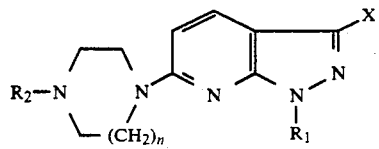

where the parameters n, $R_1$, $R_2$ and X are as defined in the specification which are selective inhibitors of the reuptake of the serotonin and as such are useful for the treatment of depression and obsessive compulsive disorder.

26 Claims, No Drawings

6-PIPERAZINYL-1H-PYRAZOLO[3,4-B]PYRIDINE-3-CARBOXYLIC ACIDS, ESTERS, AMIDES AND RELATED COMPOUNDS

The present invention relates to compounds having Formula I depicted below,

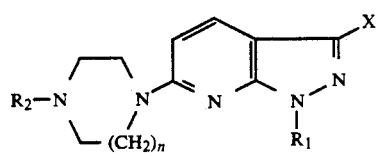
(I)

where
- n is an integer of 1 or 2;
- $R_1$ is hydrogen, loweralkyl or arylloweralkyl;
- $R_2$ is hydrogen, loweralkyl or hydroxy-substituted loweralkyl; and
- X is —H, —CN, —COOH, —COOR$_3$ or —CONR$_4$R$_5$,
  - $R_3$ being loweralkyl; $R_4$ being hydrogen, loweralkyl or arylloweralkyl; and
  - $R_5$ being hydrogen or loweralkyl;

which compounds are selective inhibitors of the reuptake of serotonin and as such are useful for the treatment of depression and obsessive compulsive disorder.

Unless otherwise stated or indicated, the following definitions shall apply throughout the specification and the appended claims.

The term loweralkyl shall mean a straight or branched alkyl group having from 1 to 6 carbon atoms. Examples of said loweralkyl include methyl, ethyl, n-propyl, isopropyl, n-butyl, iso-butyl, sec-butyl and straight- and branched-chain pentyl and hexyl.

The term aryl in each occurrence shall mean a phenyl group optionally mono-substituted with a loweralkyl, loweralkoxy, halogen, nitro or trifluoromethyl group.

The term halogen shall mean fluorine, chlorine, bromine or iodine.

Throughout the specification and the appended claims, a given chemical formula or name shall encompass all geometric, stereo, optical and tautomeric isomers where such isomers exist.

The compounds of this invention can be prepared by utilizing one or more of the synthetic steps described below.

Throughout the description of the synthetic steps, the notations n, X and $R_1$ through $R_5$ shall have the respective meanings given above unless otherwise stated or indicated.

STEP A:

2,6-Difluoropyridine is allowed to react with lithium diisopropylamide in a suitable medium such as tetrahydrofuran to afford an anion carrying a negative charge at the 3-position of the pyridine ring and this anion is allowed to react with a formylating agent depicted by Formula II to afford 2,6-difluropyridine-3-carboxaldehyde depicted by Formula III. Typically both the anion formulation and the subsequent formylation reaction are conducted at a low temperature of about −65° C.

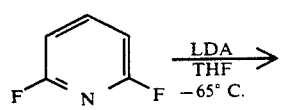

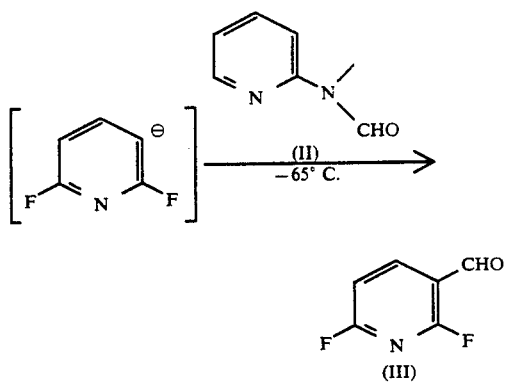
(III)

STEP B:

Compound III obtained in STEP A is allowed to react with a piperazine compound of Formula IV to afford a compound of Formula V. This reaction is typically conducted in a suitable solvent such as N-methylpyrrolidone at a temperature of about 0° C.

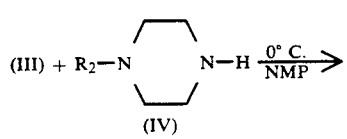

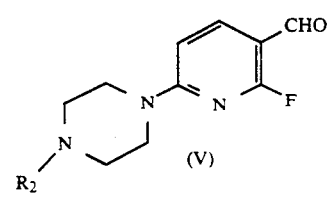
(V)

STEP C:

Compound V is allowed to react with acetyl hydrazine to afford a corresponding acetyl hydrazone of Formula VI. Typically, this reaction is conducted in a suitable solvent such as ethanol at a temperature of about 25° C.

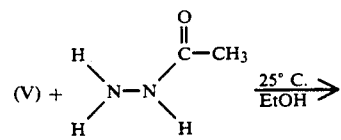

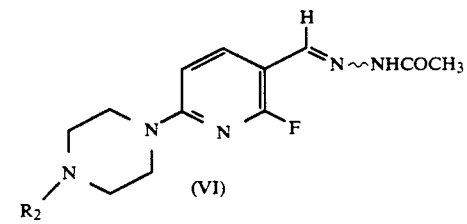
(VI)

STEP D:

The acetylhydrazone compound of Formula VI is allowed to react with a hydrazine of Formula VII to undergo a cyclization reaction to afford a compound of Formula VIII. This reaction is typically conducted at a temperature of about 90° C.

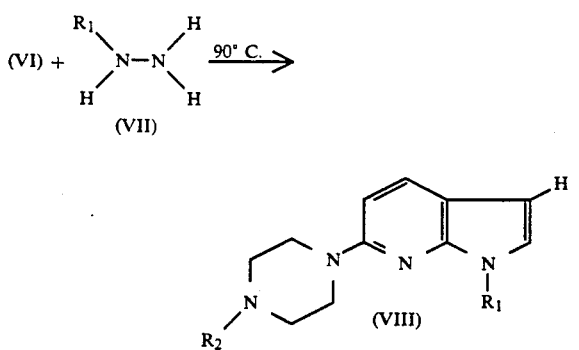

STEP E:

2,6-Difluoropyridine is allowed to react with lithium diisopropylamide in substantially the same manner as in STEP A and the resultant anion is allowed to react with t-butyl-α-oxo-1H-imidazole-1-acetate to afford a compound of Formula IX. The second reaction is typically conducted in a suitable solvent such as cyclohexane at a low temperature of about −65° C.

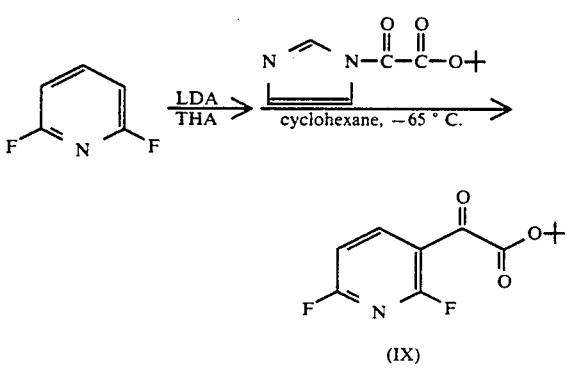

STEP F:

Compound IX is allowed to react with a hydrazine of Formula VII in the presence of Ti(O-iPr)$_4$ to afford a compound of Formula X. This reaction is typically conducted in a suitable solvent such as dichloromethane at a temperature of about 25° C.

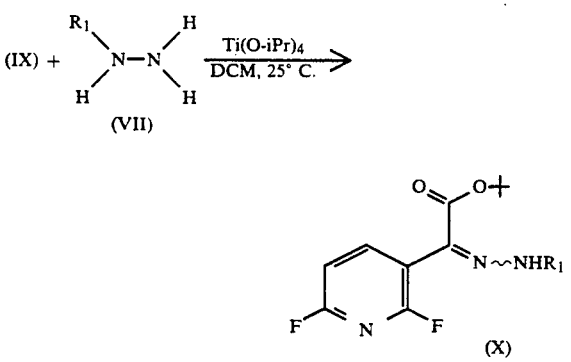

STEP G:

Compound X is allowed to undergo a cyclization in the presence of a strong base such as sodium hydride to afford a compound of Formula XI. Typically, this reaction is conducted in a suitable medium such as tetrahydrofuran at a temperature of about 25° C.

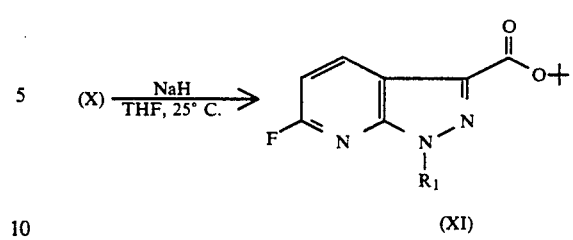

STEP H:

Compound XI is cleaved with the aid of a suitable acid such as trifluoroacetic acid to afford a corresponding carboxylic acid of Formula XII.

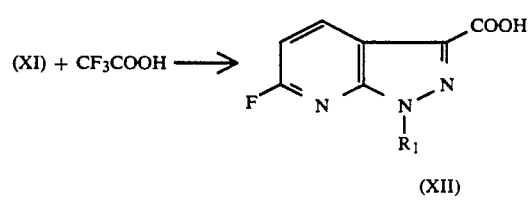

STEP I:

The carboxylic acid of Formula XII is allowed to react with 1,1'-carbonyl diimidazole and the resultant intermediate is allowed to react with ammonium acetate or an amine of the formula HNR$_4$R$_5$ (where R$_4$ is hydrogen, loweralkyl or arylloweralkyl; and R$_5$ is hydrogen or loweralkyl; but both R$_4$ and R$_5$ may not be hydrogen) to afford a compound of Formula XIII. The first step is typically conducted in a suitable solvent such as dimethylformamide at a temperature of about 25° C. and the second step is also conducted at a temperature of about 25° C.

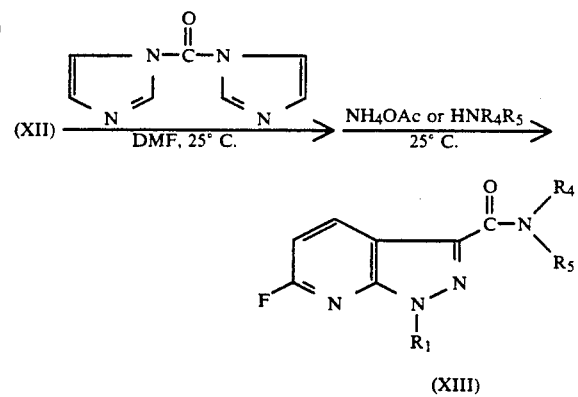

STEP J:

The amide compound of Formula XIII is allowed to react with the aforementioned piperazine compound of Formula IV to afford a compound of Formula XIV. This reaction is conducted in substantially the same manner as in STEP B.

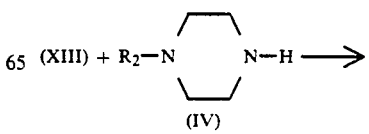

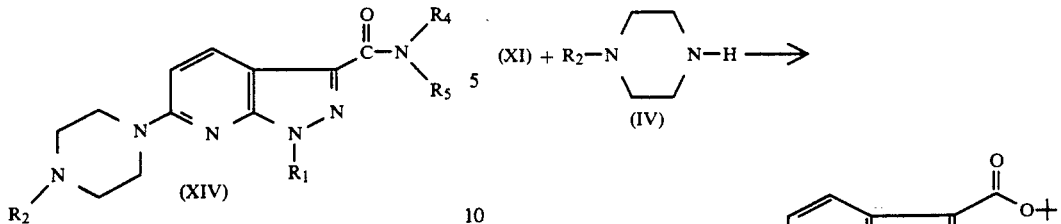

STEP K:

Compound XIIIa obtained from STEP I is allowed to react with trifluoroacetic anhydride to afford a nitrile compound of Formula XV. This reaction is typically conducted in a suitable medium such as a pyridine/THF mixture at a temperature of about 25° C.

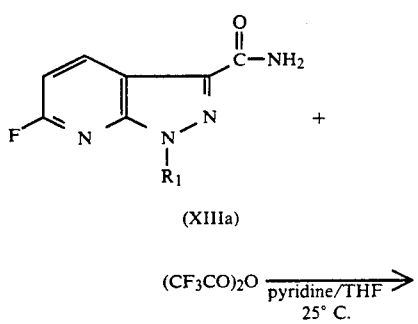

STEP L:

The nitrile compound of Formula XV is allowed to react with the piperazine compound of Formula IV in substantially the same manner as in STEP J to afford a compound of Formula XVI.

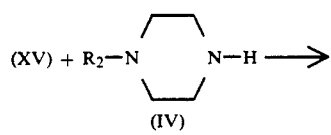

STEP M:

Compound XI is allowed to react with the piperazine compound of Formula IV in substantially the same manner as in STEP J to afford a compound of Formula XVII.

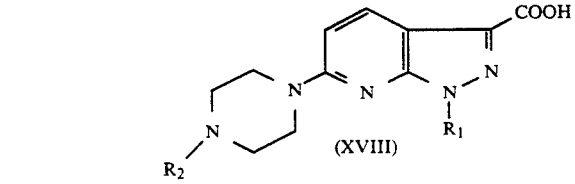

STEP N:

Compound XVII is cleaved in substantially the same manner as in STEP H to afford a compound of Formula XVIII.

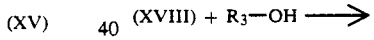

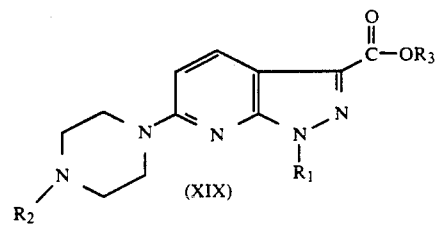

STEP O:

Compound XVIII is esterified with an alcohol of the formula $R_3$-OH, where $R_3$ is as defined earlier, to afford a corresponding ester compound of Formula XIX.

(XVIII) + $R_3$—OH ⟶

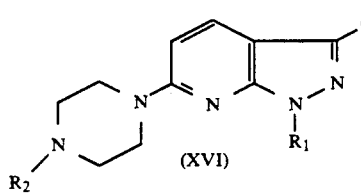

The compounds of Formula I of the present invention are useful for the treatment of depression and obsessive compulsive disorder. This utility is demonstrated by the activities of these compounds as selective inhibitors of the reuptake of serotonin. Said activities are ascertained according to the protocol described below.

[$^3$H]-Serotonin Uptake in Rat Whole Brain and Hypothalamic Synaptosomes

This assay is used as a biochemical screen for compounds which block serotonin (5HT) uptake, which may be useful as antidepressants and for the the treatment of personality disorders such as obsessive compulsive disorder.

Procedure:

A. Animals: Male CR Wistar rats (100–125 g).

B. Reagents

1. Krebs-Henseleit Bicarbonate Buffer, pH 7.4 (KHBB):

Prepare a 1 liter batch, containing the following salts.

|  | g/L | mM |
|---|---|---|
| NaCl | 6.92 | 118.4 |
| KCl | 0.35 | 4.7 |
| MgSO$_4$.7H$_2$O | 0.29 | 1.2 |
| KH$_2$PO$_4$ | 0.16 | 2.2 |
| NaHCO$_3$ | 2.10 | 24.9 |
| CaCl$_2$ | 0.14 | 1.3 |

Prior to use add to 200 ml, per assay:

| Dextrose | 2 mg/ml | 11.1 |
|---|---|---|
| Iproniazid phosphate | 0.30 mg/ml | 0.1 |

The batch is aerated for 60 min. with 95% O$_2$/5% CO$_2$, check pH (7.4±0.1), then add bovine serum albumin (Sigma ca# A-7906) 1 mg/ml.

2. Filtration buffer:
Make a 4 liter batch, containing the following salts:

|  | g/4L | mM |
|---|---|---|
| NaCl | 31.68 | 135.5 |
| KCl | 1.40 | 4.7 |
| MgSO$_4$.7H$_2$O | 1.16 | 1.2 |
| HEPES | 1.16 | 10.0 |
| CaCl$_2$ | 0.56 | 1.3 |
| BSA | 4.0 | 1 mg/ml |

Maintain on ice.

3. Sucrose solution: 0.32M sucrose containing 5 mM HEPES and 0.1 mM EDTA; pH to 7.3 using Tris base.

4. A 0.1 mM stock solution of serotonin creatinine SO$_4$ is made up in 0.01N HCl. This is used to dilute the specific activity of the radiolabeled 5HT.

5. 5-[1,2-$^3$H(N)]-Hydroxytryptamine creatinine sulfate (Serotonin), specific activity 20–30 Ci/mmol, is used.

The final desired concentration of [$^3$H]-5HT in the assay is 50 nM. The dilution factor is 0.8. The KHBB is made up to contain 62.5 nM [$^3$H]-5HT.
Add to 100 ml of KHBB.

| A) 56.1 μl of 0.1 mM 5HT | = | 56.1 nM |
|---|---|---|
| B) 0.64 nmole of $^3$H-5HT | = | 6.4 nM |
|  |  | 62.5 nM |

6. For most assays, a 0.5 mM stock solution of the test compound is made up initially in either 10 μl of glacial acetic acid, 100 μl DMSO or 10 μl of the recrystallization solvent, to which is added approximately 10 ml of distilled water. Compounds are initially screened in duplicate at 3 concentrations ($10^{-8}$, $10^{-7}$ and $10^{-6}$M) made up in water. For those compounds demonstrating activity at $\leq 10^{-7}$ in the initial screen, EC$_{50}$s are determined from 7 concentrations: $10^{-9}$ through $10^{-6}$. Higher or lower concentration ranges may be used depending on the potency of the compound. To ensure consistency, the standard chlomipramine is run with each assay.

C. Tissue Preparation

The Percoll method for preparing synaptosomes has been modified by Nagy, A., Delgado-Escueta, A. V. J. Neurochem. 43, 1114 (1984) and Dunkley, P. R., Jarvie, R. E., Heath, J. W., Kidd, G. J., Rostas, J. A. P. Brain Research 372, 115 (1986). Male Wistar rats are decapitated and the brain rapidly removed. Whole brain minus cerebella is weighed and homogenized in 15 volumes of ice-cold sucrose solution using a Potter-Elvejhem homogenizer. The following procedures are performed on ice. Homogenization should be done with 4–5 up and down strokes at medium speeds (setting 4.5 to 5) to minimize synaptosome lysis. The homogenate is centrifuged at 1000 g (3000 rpm, Sorval SS-34 rotor) for 10 min. at 0°–4° C. The supernatant (S$_1$) is removed and approximately 10 ml per tube is carefully layered onto a discontinuous Percoll (Sigma ca# P-1644) gradient: 21% Percoll in Sucrose solution at the bottom (15 ml per tube) and 10% Percoll in the middle (10 ml; colored with a few drops of phenol red for visiblity).

The Percoll gradient tubes are carefully placed into a Beckman SW-28 swinging bucket rotor and spun in a Beckman XL90 ultracentrifuge using the following program: speed, 11,000 rpm for 30 minutes at 4° C.; slow acceleration and deceleration (acceleration setting 9; deceleration setting 3). Tubes are carefully removed, and the top layer and the top part of the middle (red) layer are discarded using a pasteur pipette. The synaptosomes are located in the white fluffy band at the interface between 10% and 21% Percoll layers. This is carefully removed, placed in a centrifuge tube, diluted with KHBB and spun at 21,000 g (13,000 rpm, Sorvall SS-34 rotor). The pellet (synaptosomes) is resuspended in KHBB (10 vol per gram original brain wet weight; 1 brain minus cerebellum weights approximately 1.2 g; 2.5 brains are needed per typical assay).

D. Assay

800 μl KHBB with [$^3$H]-5HT
20 μl Vehicle or appropriate drug concentration
200 μl Tissue suspension concentration 200 μl of the tissue suspension are added to each of 24 tubes (at a time) containing the 20 μl of vehicle or drug on ice. Three minutes later, 800 μl of KHBB containing [$^3$H]-5HT are added, and the tubes are vortexed. The rack containing the 24 tubes is removed from the ice batch to a water bath set at 37° C. The tubes are incubated at 37° C. under a 95% O$_2$/5% CO$_2$ atmosphere for 5 minutes. Uptake is terminated by filtration through GF/B filter strips using a Brandel cell harvester (filter strips are presoaked in ice cold filtration buffer). Tubes are washed once with 5 ml of ice cold filtration buffer. Filter disks are placed in scintillation vials to which are added 10 ml of scintillation fluid (EcoScint). Filters are allowed to sit overnight before being counted.

For each assay, 3 tubes are incubated with 20 μl of vehicle at both 37° C. and 0° C. Active uptake is the difference between cpm taken up at 37° C. and 0° C. Percent inhibition at each concentration is the mean of two determinants. IC$_{50}$ values are derived from log probit analysis using #46 Litchfield and Wilcoxon I: confidence limits of IC$_{50}$ Pharmacologic Calculation System-version 4.0.

The results of the above test procedure expressed in terms of IC$_{50}$ are presented in Table 1 for some of the compounds of this invention along with data measured in the same way for reference compounds, amitriptyline and fluoxetine.

TABLE 1

| Inhibition of Serotonin Uptake | |
|---|---|
| Compound | IC$_{50}$($10^{-6}$M) |
| 6-(1-piperazinyl)-1H-pyrazolo [3,4-b]pyridine-3-carboxamide | 7.69 |

TABLE 1-continued

| Inhibition of Serotonin Uptake | |
|---|---|
| Compound | $IC_{50}(10^{-6}M)$ |
| hydrochloride hydrate | |
| 6-(4-methyl-1-piperazinyl)-1H-pyrazolo[3,4-b]pyridine-3-carbonitrile | 0.764 |
| 6-(1-piperazinyl)-1H-pyrazolo[3,4-b]pyridine-3-carbonitrile | 0.696 |
| 6-(1-hexahydro-1H-1,4-diazepin-1-yl)-1H-pyrazolo[3,4-b]pyridine-3-carbonitrile | 0.349 |
| 1-methyl-6-(4-methyl-1-piperazinyl)-1H-pyrazolo[3,4-b]pyridine | 3.43 |
| 6-(4-methyl-1-piperazinyl)-1H-pyrazolo[3,4-b]pyridine | 8.26 |
| (Reference Compounds) | |
| Amitriptyline | 0.091 |
| Fluoxetine | 0.048 |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0-300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweeting agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds according to this invention include:

6-(4-methyl-1-piperazinyl)-1H-pyrazolo[3,4-b]pyridine;
1-methyl-6-(4-methyl-1-piperazinyl)-1H-pyrazolo[3,4-b]pyridine;
t-butyl 6-(1-piperazinyl)-1H-pyrazolo[3,4-b]pyridine-3-carboxylate;
t-butyl 6-(4-methyl-1-piperazinyl)-1H-pyrazolo[3,4-b]pyridine-3-carboxylate;
6-(4-methyl-1-piperazinyl)-1H-pyrazolo[3,4-b]pyridine-3-carboxylic acid;
6-(1-piperazinyl)-1H-pyrazolo[3,4-b]pyridine-3-carboxylic acid;
methyl 6-(4-methyl-1-piperazinyl)-1H-pyrazolo[3,4-b]pyridine-3-carboxylate;
6-(1-piperazinyl)-1H-pyrazolo[3,4-b]pyridine-3-carboxamide;
6-(4-methyl-1-piperazinyl)-1H-pyrazolo[3,4-b]pyridine-3-carboxamide;
6-(1-piperazinyl)-1H-pyrazolo[3,4-b]pyridine-3-carbonitrile;
6-(4-methyl-1-piperazinyl)-1H-pyrazolo[3,4-b]pyridine-3-carbonitrile;
6-(hexahydro-1H-1,4-diazepin-1-yl-1H-pyrazolo[3,4-b]pyridine-3-carbonitrile; and
6-(4-(2-hydroxyethyl)-1-piperazinyl)-1H-pyrazolo[3,4-b]pyridine-3-carbonitrile;

The following examples are presented in order to illustrate the present invention.

EXAMPLE 1

2-Fluoro-6-(4-methyl-1-piperazinyl)pyridine-3-carboxaldehyde

Part (a):

Diisopropylamine (7.80 g, 0.077 mole) was dissolved in 40 mL of THF and the solution was chilled at −70° C. n-Butyllithium was added dropwise (48 mL of 1.6M, 0.077 mole) and then stirring was continued for 30 minutes. At the end of this time, 2,6-difluoropyridine (8.03 g, 0.07 mole) was added and stirring was continued for 2 hours. N-Methyl-N-(2-pyridinyl)formamide[a] (9.5 g, 0.07 mole) was then added and the reaction mixture was allowed to come to room temperature. It was distributed between diethyl ether and 5% aqueous HCl and the organic phase was separated, dried, and concentrated to give an oil which was purified by flash chromatography (40% pentane-$CH_2Cl_2$) to give, after concentration of the product-containing fractions, 4.89 g, (49%) of 2,6-difluoropyridine-3-carboxaldehyde as a somewhat volatile oil.

[a]Synthesis, 1978, 403.

Part (b):

2,6-Difluoropyridine-3-carboxaldehyde (4.89 g, 0.034 mole) was dissolved in 20 mL of N-methylpyrrolidone and chilled in an ice/water bath. N-methylpiperazine (3.5 g, 0.035 mole) was added dropwise and the reaction mixture was stirred for 15 minutes and then distributed between 5% NaOH and $Et_2O$. The organic phase was dried and concentrated to give 6.25 g (82%) of product. An analytical sample was obtained by recrystallization from pentane, mp 77°–78° C.

Analysis: Calculated for $C_{11}H_{14}FN_3O$: 59.18% C; 6.32% H; 18.82% N; Found: 58.97% C; 6.31% H; 18.95% N.

EXAMPLE 2

2-Fluoro-6-(4-methyl-1-piperazinyl)pyridine-3-carboxaldehyde acetylhydrazone

2-Fluoro-6-(4-methyl-1-piperazinyl)pyridine-3-carboxaldehyde (3.35 g, 0.015 mole) was dissolved in 20 mL of EtOH and treated with acetylhydrazine (2.2 g, 0.030 mole). This reaction mixture was stirred for 72 hours and then the product was filtered off and recrystallized from EtOAc to give 2.85 g, mp 210°–212° C.

Analysis: Calculated for $C_{11}H_{14}FN_3O$: 55.90% C; 6.50% H; 25.07% N; Found: 55.88% C; 6.43% H; 25.14% N.

EXAMPLE 3

6-(4-Methyl-1-piperazinyl)-1H-pyrazolo[3,4-b]pyridine

2-Fluoro-6-(4-methyl-1-piperazinyl)pyridine-3-carboxaldehyde acetylhydrazone (2.30 g, 8.23 mmole) was warmed at 90° C. in 20 mL of hydrazine hydrate. After 30 minutes, water was added to the reaction mixture and the product was filtered off. The aqueous filtrate was concentrated under reduced pressure and the resulting solid triturated with water. This product was combined with the product that had been previously filtered off and the two were recrystallized together from EtOAc, giving 1.15 g, (64%), mp 196°–197° C.

Analysis: Calculated for $C_{11}H_{15}N_5$: 60.81% C; 6.96% H; 32.23% N; Found: 60.80% C; 6.98% H; 32.50% N.

EXAMPLE 4

1-Methyl-6-(4-methyl-1-piperazinyl)-1H-pyrazolo[3,4-b]pyridine

2-Fluoro-6-(4-methyl-1-piperazinyl)pyridine-3-carboxaldehyde acetylhydrazone (2.30 g, 8.23 mmole) was warmed at 90° C. in 10 mL of methylhydrazine. After 30 minutes the reaction mixture was concentrated under reduced pressure and the resulting solid triturated with water. The product was filtered off and the aqueous filtrate was extracted three times with $CH_2Cl_2$. The $CH_2Cl_2$ was evaporated and the residual product was combined with the product that had been previously filtered off and the two were recrystallized together from pentane, giving 1.37 g (72%), mp 106°–107° C.

Analysis: Calculated for $C_{12}H_{17}N_5$: 62.31% C; 7.41% H; 30.28% N; Found: 62.29% C; 7.32% H; 30.37% N.

EXAMPLE 5 t-Butyl 2,6-Difluoropyridine-3-(α-oxoacetate)

2,6-Difluoropyridine (23.0 g, 0.20 mole) was dissolved in 200 mL of THF and chilled to −65° C. A 1.5M solution of lithium diisopropylamide/THF complex in cyclohexane (140 mL, 0.21 mole) was then added and the reaction mixture was stirred for 30 minutes in the cold. In a separate flask, a solution of t-butyl α-oxo-1H-imidazole-1-acetate[a](49.0 g, 0.25 mole) in 200 mL of THF was chilled to −65° C. and to this the first solution was slowly added by a positive pressure of nitrogen through a Teflon cannula. The combined solution was stirred in the cold for 30 minutes and then allowed to come to room temperature over 45 minutes. At the end of this time the reaction mixture was distributed between diethyl ether and saturated aqueous ammonium chloride solution and then the organic layer was separated and dried. The product obtained upon concentration of the organic layer was purified by preparative high pressure liquid chromatography (10% ethyl acetate-heptane, 150 mL/min) to give 24.3 g (50%) of t-butyl 2,6-difluoropyridine-3-(α-oxoacetate) as an oil.

[a]J. Org. Chem. 46, 211 (1981).

EXAMPLE 6 t-Butyl 6-Fluoro-1H-pyrazolo[3,4-b]pyridine-3-carboxylate 2,6-Difluoropyridine-3-(α-oxo)acetic acid, t-butyl ester (11.45 g, 0.047 mole) was dissolved in 50 mL of $CH_2Cl_2$ to which were then added sequentially Ti(O-iPr)$_4$ (26.7 g, 0.094 mole) and hydrazine hydrate (4.7 g, 0.094 mole). The reaction mixture was stirred vigorously for 1 hour and then 11 mL of $H_2O$ was added and stirring was continued overnight. It was filtered through Celite and concentrated to give crude hydrazone, which was used without further purification.

The hydrazone obtained in this fashion was dissolved in 100 mL THF and treated with 2.0 g of 60% NaH (0.050 mole). After 20 minutes the reaction mixture was distributed between 5% HCl and $Et_2O$ and the organic phase separated and dried. Further purification by flash chromatography (10% EtOAc/$CH_2Cl_2$) gave 5.30 g of product (47.5% for the two steps). Analytically pure material was obtained by recrystallization from $CH_2Cl_2$/heptane, mp 183°–185° C.

Analysis: Calculated for $C_{11}H_{12}FN_3O$: 55.69% C; 5.10% H; 17.71% N; Found: 55.66% C; 5.09% H; 17.90% N.

EXAMPLE 7 t-Butyl 6-(1-piperazinyl)-1H-pyrazolo[3,4-b]pyridine-3-carboxylate t-Butyl 6-fluoro-1H-pyrazolo[3,4-b]pyridine-3-carboxylate (3.00 g, 0.0126 mole) was dissolved in 100 mL of toluene containing 10.85 g of piperazine (0.126 mole) and refluxed overnight. The resultant precipitate was filtered off and distributed between an aqueous NaHCO$_3$ solution and EtOAc and then the organic phase was dried and concentrated to give a product which was recrystallized from $CH_3CN$ to give 1.57 g, mp 190°–191° C. The toluene filtrate was washed with NaHCO$_3$ solution and then concentrated and purified by flash chromatography (EtOAc:MeOH:Et₃N/16:2:2) to give an additional 1.38 g of product (total yield 77%).

Analysis: Calculated for $C_{15}H_{21}N_5O_2$: 59.39% C; 6.98% H; 23.09% N; Found: 59.28% C; 6.99% H; 23.14% N.

EXAMPLE 8 t-Butyl 6-(4-Methyl-1-piperazinyl)-1H-pyrazolo[3,4-b]pyridine-3-carboxylate t-Butyl 6-fluoro-1H-pyrazolo[3,4-b]pyridine-3-carboxylate (1.37 g, 5.77 mmole) was dissolved in 20 mL of toluene containing 1.44 g of N-methylpiperazine (14.4 mmole) and refluxed overnight. An additional 1.0 g of N-methylpiperazine (10 mmole) was added at this time and reflux was continued for additional 24 hours. The reaction mixture was concentrated and the residue was purified by flash chromatography (EtOAc:MeOH:Et₃N/18:1:1) to give 1.19 g of product (65%). Analytically pure material was obtained by recrystallization from CH₃CN, mp 189°–190° C.

Analysis: Calculated for $C_{16}H_{23}N_5O_2$: 60.55% C; 7.30% H; 20.07% N; Found: 60.38% C; 7.17% H; 22.07% N.

EXAMPLE 9

6-(4-Methyl-1-piperazinyl)-1H-pyrazolo[3,4-b]pyridine-3-carboxylate acid trifluoroacetate t-Butyl 6-(4-methyl-1-piperazinyl)-1H-pyrazolo[3,4-b]pyridine-3-carboxylate (2.15 g, 6.77 mmole) was dissolved in 35 mL of trifluoroacetic acid and allowed to stand undisturbed for 1 hour. The solvent was then evaporated and the residue recrystallized from MeOH-Et₂O to give 1.37 g (53.9%) of analytically pure product, mp 236° C. (dec).

Analysis: Calculated for $C_{12}H_{15}N_5O_2 \cdot C_2HF_3O_2$: 44.80% C; 4.30% H; 18.66% N; Found: 44.67% C; 4.28% H; 18.54% N.

EXAMPLE 10

6-(1-Piperazinyl)-1H-pyrazolo[3,4-b]pyridine-3-carboxylic trifluoroacetate hemihydrate t-Butyl 6-(1-piperazinyl)-1H-pyrazolo[3,4-b]pyridine-3-carboxylate (1.76 g, 5.80 mmole) was dissolved in 35 mL of trifluoroacetic acid and allowed to stand undistributed for 1 hour. The solvent was then evaporated and the residue recrystallized from MeOH-Et₂O to give 1.08 g (50.0%) of analytically pure product, mp 335° C. (dec).

Analysis: Calculated for $C_{12}H_{15}N_5O_2 \cdot C_2HF_3O_2 \cdot 0.5 H_2O$: 42.15% C; 4.08H; 18.91% N; Found: 42.22% C; 3.92% H; 18.78% N.

EXAMPLE 11

Methyl 6-(4-methyl-1-piperazinyl)-1H-pyrazolo[3,4-b]pyridine-3-carboxylate 6-(4-Methyl-1-piperazinyl)-1H-pyrazolo[3,4-b]pyridine-3-carboxylate trifluoroacetate (1.82 g, 4.8 mmole) was refluxed overnight in 300 mL of MeOH containing 2 mL of concentrated H₂SO₄. The reaction mixture was concentrated to ca. 100 mL and then distributed between EtOAc and an aqueous NaHCO₃ solution. The aqueous phase was extracted additional two times with EtOAc and then the combined organic phase was dried and concentrated. Recrystallization from MeOH gave 1.21 g (91%) of analytically pure product, mp 230°–231° C.

Analysis:
Analysis: Calculated for $C_{13}H_{17}N_5O_2$: 56.72% C; 6.22% H; 25.44% N; Found: 56.84% C; 6.19% H; 25.34% N.

EXAMPLE 12

6-Fluoropyrazolo[3,4-b]pyridine-3-carboxamide t-Butyl 6-fluoro-1H-pyrazolo[3,4-b]pyridine-3-carboxylate (8.90 g, 37.5 mmole) was dissolved in 30 mL of trifluoroacetic acid and allowed to stand undisturbed for 2 hours. The solvent was then evaporated and the residue was dissolved in 30 mL of DMF. N,N'-Carbonyldiimidazole (7.0 g, 43.2 mmol) was added and the reaction mixture was stirred overnight. Ammonium acetate (8.7 g, 113 mmol) was then added to the resulting suspendion and stirring was continued for 4 hours. The solvent was evaporated under high vacuum and the residue was triturated well with H₂O to give 6.02 g (89%) of product after drying. An analytical sample was obtained by recrystallization from HOAc, mp 295° C. (dec).

Analysis: Calculated for $C_7H_5FN_4O$: 46.67% C; 2.80% H; 31.10% N; Found: 46.40% C; 2.75% H; 30.78% N.

EXAMPLE 13

6-(1-Piperazinyl)-1H-pyrazolo[3,4-b]pyridine-3-carboxamide hydrochloride hydrate 6-Fluoropyrazolo[3,4-b]pyridine-3-carboxamide (2.0 g, 11.0 mmole) was suspended in 15 mL of NMP and then piperazine (9.5 g, 110 mmole) was added. The reaction was warmed at 85° for 90 minutes and then the solvent was evaporated under high vacuum and the residue was triturated sequentially with 10% NaOH and MeOH to give 2.20 g (81.5%) of product. The hydrochloride was formed in concentrated HCl and crystallized by the addition of CH₃CN, mp 350° C.

Analysis: Calculated for $C_{11}H_{14}N_6O \cdot HCl \cdot H_2O$: 43.93% C; 5.70% H; 27.94% N; Found: 43.69% C; 5.36% H; 28.25% N.

EXAMPLE 14

6-(4-Methyl-1-piperazinyl)-1H-pyrazolo[3,4-b]pyridine-3-carboxamide maleate

6-Fluoropyrazolo[3,4-b]pyridine-3-carboxamide (2.00 g, 11.0 mmole) was dissolved in 7 mL of N-methylpyrrolidone containing N-methylpiperazine (4.4 g, 44.0 mmole). The reaction mixture was warmed at 85° C. for 4 hours and then the precipitated hydrofluoride was filtered off and stirred overnight in 10% NaOH. It was again filtered off and washed with H₂O. The maleate was formed in MeOH and recrystallized from MeOH/H₂O to give 1.71 g (41.3%), mp 230° C. (dec).

Analysis: Calculated for $C_{12}H_{16}N_6O \cdot C_4H_4O_4$: 51.06% C; 5.36% H; 22.33% N; Found: 50.98% C; 5.49% H; 22.65% N.

EXAMPLE 15

6-Fluoro-1H-pyrazolo[3,4-b]pyridine-3-carbonitrile

6-Fluoro-1H-pyrazolo[3,4-b]pyridine-3-carboxamide (10.3 g, 57.0 mmole) was suspended in 75 mL of THF and thereafter pyridine (14.2 mL, 180 mmole) was added, followed by the dropwise addition of trifluoroacetic anhydride (25.2 mL, 180 mmole). The reaction mixture was stirred for two hours at room temperature and then distributed between EtOAc and H₂O. The organic phase was concentrated and the crude product was purified by flash chromatography (5% EtOAc-CH₂Cl₂). Concentration of the product-containing fractions gave 8.72 g of product (94.4%). An analytical sample was obtained by recrystallization from EtOAc-pentane, mp 172°–173°.

Analysis: Calculated for C₇H₃FN₄: 51.86% C; 1.87% H; 34.56% N; Found: 51.60% C; 1.74% H; 34.55% N.

EXAMPLE 16

6-(1-Piperazinyl)-1H-pyrazolo[3,4-b]pyridine-3-carbonitrile

6-Fluoro-1H-pyrazolo[3,4-b]pyridine-3-carbontrile (1.62 g, 10.0 mmole) was dissolved in 20 mL of N-methylpyrrolidone. Piperazine (4.3 g, 50.0 mmole) was added and the reaction mixture was warmed for two hours at 80° C. It was poured into H₂O and then the product was filtered off and recrystallized from MeOH-H₂O to give 1.77 g (77.6%) of analytically pure product, mp 273°(dec).

Analysis: Calculated for C₁₁H₁₂N₆: 57.88% C; 5.30% H; 36.82% N; Found 57.83% C; 5.01% H; 36.92% N.

EXAMPLE 17

6-(4-Methyl-1-piperazinyl)-1H-pyrazolo[3,4-b]pyridine-3-carbonitrile

6-Fluoro-1H-pyrazolo[3,4-b]pyridine-3-carbonitrile (1.62 g, 10.0 mmole) was dissolved in 20 mL of N-methylpyrrolidone. N-methylpiperazine (3.0 g, 30.0 mmole) was added and the reaction mixture was warmed for 2 hours at 80°. It was poured into H₂O and then the product was filtered off and recrystallized from MeOH-H₂H₂O to give 1.41 g (58%) of analytically pure product, mp 255°(dec).

Analysis: Calculated for C₁₂H₁₄N₆: 59.49% C; 5.82% H; 34.69% N; Found: 59.33% C; 5.77% H; 34.84% N.

EXAMPLE 18

6-(Hexahydro-1H-1,4-diazepin-1-yl)-1H-pyrazolo[3,4-b]pyridine-3-carbonitrile

6-Fluoro-1H-pyrazolo[3,4-b]pyridine-3-carbonitrile (1.62 g, 10.0 mmole) was dissolved in 20 mL of N-methylpyrrolidone. Hexahydro-1H-1,4-diazepine (5.0 g, 50.0 mmole) was added and then the reaction mixture was warmed for 2 hours at 80°. It was poured into H₂O and then the product was filtered off and recrystallized from MeOH-H₂O to give 1.32 g (54.5%) of analytically pure product, mp 196°–197°.

Analysis: Calculated for C₁₂H₁₄N₆: 59.49% C; 5.82% H; 34.69% N; Found: 59.43% C; 5.62% H; 34.64% N.

EXAMPLE 19

6-(4-(2-Hydroxyethyl)-1-piperazinyl)-1H-pyrazolo[3,4-b]pyridine-3-carbonitrile

6-Fluoro-1H-pyrazolo[3,4-b]pyridine-3-carbonitrile (0.81 g, 5.00 mmole) was warmed at 90° C. in 10 mL of N-methylpyrrolidone (NMP) containing 1.95 g (15 mmole) of 1-(2-hydroxyethyl)piperazine. After 20 minutes the reaction mixture was poured into H₂O and the product was filtered off. Recrystalliazation from MeOH-H₂O gave 1.12 g (82%) of analytically pure product, mp 232°–233°.

Analysis: Calculated for C₁₃H₁₆N₆O: 57.34% C; 5.92% H; 30.86% N; Found: 57.13% C; 5.94% H; 30.72% N.

We claim:

1. A compound of the formula

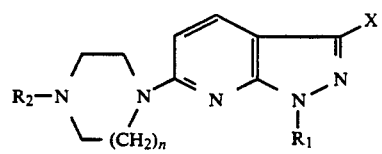

where
n is an integer of 1 or 2;
R₁ is hydrogen, loweralkyl or arylloweralkyl;
R₂ is hydrogen, loweralkyl or hydroxy-substituted loweralkyl; and
X is —H, —CN, —COOH, —COOR₃ or —CONR₄R₅,
R₃ being loweralkyl; R₄ being hydrogen, loweralkyl or arylloweralkyl; and
R₅ being hydrogen or loweralkyl;
or a pharmaceutically acceptable acid addition salt thereof.

2. The compound as defined in claim 1, where n is 1.

3. The compound as defined in claim 1, where R₁ is hydrogen or loweralkyl.

4. The compound as defined in claim 1, where n is 1, and R₁ is hydrogen or loweralkyl.

5. The compound as defined in claim 1, where X is —H, —CN, —COOH, —COOR₃ or —CONH₂.

6. The compound as defined in claim 1, where n is 1, and X is —H, —CN, —COOH, —COOR₃ or —CONH₂.

7. The compound as defined in claim 1, where n is 2.

8. The compound as defined in claim 7, where R₁ is hydrogen or loweralkyl.

9. The compound as defined in claim 8, where R₂ is hydrogen or loweralkyl.

10. The compound as defined in claim 9, where X is —H, —CN, —COOH, —COOR₃ or —CONH₂.

11. The compound as defined in claim 1, which is 6-(4-methyl-1-piperazinyl)-1H-pyrazolo[3,4-b]pyridine.

12. The compound as defined in claim 1, which is 1-methyl-6-(4-methyl-1-piperazinyl)-1H-pyrazolo[3,4-b]pyridine.

13. The compound as defined in claim 1, which is t-butyl 6-(1-piperazinyl)-1H-pyrazolo[3,4-b]pyridine-3-carboxylate.

14. The compound as defined in claim 1, which is t-butyl 6-(4-methyl-1-piperazinyl)-1H-pyrazolo[3,4-b]pyridine-3-carboxylate.

15. The compound as defined in claim 1, which is 6-(4-methyl-1-piperazinyl)-1H-pyrazolo[3,4-b]pyridine-3-carboxylic acid.

16. The compound as defined in claim 1, which is 6-(1-piperazinyl)-1H-pyrazolo[3,4-b]pyridine-3-carboxylic acid.

17. The compound as defined in claim 1, which is methyl 6-(4-methyl-1-piperazinyl)-1H-pyrazolo[3,4-b]pyridine-3-carboxylate.

18. The compound as defined in claim 1, which is 6-(1-piperazinyl)-1H-pyrazolo[3,4-b]pyridine-3-carboxamide.

19. The compound as defined in claim 1, which is 6-(4-methyl-1-piperazinyl)-1H-pyrazolo[3,4-b]pyridine-3-carboxamide.

20. The compound as defined in claim 1, which is 6-(1-piperazinyl)-1H-pyrazolo[3,4-b]pyridine-3-carbonitrile.

21. The compound as defined in claim 1, which is 6-(4-methyl-1-piperazinyl)-1H-pyrazolo[3,4-b]pyridine-3-carbonitrile.

22. The compound as defined in claim 1, which is 6-(hexahydro-1H-1,4-diazepin-1-yl)-1H-pyrazolo[3,4-b]pyridine-3-carbonitrile.

23. The compound as defined in claim 1, which is 6-(4-(2-hydroxyethyl)-1-piperazinyl)-1H-pyrazolo[3,4-b]pyridine-3-carbonitrile.

24. A pharmaceutical composition comprising a compound as defined in claim 1 in an amount effective for the treatment of depression or for the treatment of obsessive compulsive disorder and a suitable carrier therefor.

25. A method for treating a patient in need of relief from depression which comprises administering to such a patient an effective amount of a compound as defined in claim 1.

26. A method of treating a patient in need of relief from obsessive compulsive disorder which comprises administering to such a patient as effective amount of a compound as defined in claim 1.

* * * * *